(12) United States Patent
Lee et al.

(10) Patent No.: US 12,420,109 B2
(45) Date of Patent: Sep. 23, 2025

(54) LIFTING BAND

(71) Applicant: AMOLIFESCIENCE CO., LTD., Seoul (KR)

(72) Inventors: Hyo Jung Lee, Seoul (KR); In Yong Seo, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 464 days.

(21) Appl. No.: 17/999,037

(22) PCT Filed: May 12, 2021

(86) PCT No.: PCT/KR2021/005963
§ 371 (c)(1),
(2) Date: Nov. 16, 2022

(87) PCT Pub. No.: WO2021/235766
PCT Pub. Date: Nov. 25, 2021

(65) Prior Publication Data
US 2023/0218921 A1  Jul. 13, 2023

(30) Foreign Application Priority Data
May 18, 2020  (KR) .......................... 10-2020-0058944

(51) Int. Cl.
*A61N 5/06* (2006.01)
*A45D 44/22* (2006.01)
*A61F 7/00* (2006.01)

(52) U.S. Cl.
CPC ............ *A61N 5/0616* (2013.01); *A61F 7/007* (2013.01); *A45D 44/22* (2013.01);
(Continued)

(58) Field of Classification Search
CPC .... A61N 2005/0647; A61N 2005/0652; A61N 2005/0659; A61N 2005/0662;
(Continued)

(56) References Cited

U.S. PATENT DOCUMENTS

2019/0015679 A1*  1/2019  Taboada ............... A61N 5/0613

FOREIGN PATENT DOCUMENTS

| KR | 10-2011-0001704 A | 1/2011 |
| KR | 10-1526462 B1 | 6/2015 |

(Continued)

OTHER PUBLICATIONS

International Search Report for PCT/KR2021/005963 by Korean Intellectual Property Office dated Sep. 6, 2021.
(Continued)

*Primary Examiner* — Mohamed G Gabr
(74) *Attorney, Agent, or Firm* — BROADVIEW IP LAW, PC

(57) ABSTRACT

The present invention relates to a lifting band comprising: a band member provided in the form of a plate having elasticity and resilience and having a predetermined area; at least one light source part disposed on one surface of the band member and including a plurality of LEDs that, when power is applied, emit light of a predetermined wavelength band so as to improve the skin; and a cover member which is fixed to one surface of the band member so as to cover the at least one light source part.

18 Claims, 14 Drawing Sheets

(52) U.S. Cl.
CPC ............. *A61F 2007/0003* (2013.01); *A61F 2007/0052* (2013.01); *A61N 2005/0647* (2013.01); *A61N 2005/0652* (2013.01)

(58) Field of Classification Search
CPC .......... A61N 2005/0663; A61N 5/0616; A61N 5/0624; A61F 2007/0003; A61F 2007/0004; A61F 2007/0052; A61F 2007/0231; A61F 7/007; A61F 7/02; A45D 44/22
See application file for complete search history.

(56) References Cited

FOREIGN PATENT DOCUMENTS

| KR | 10-1782974 B1 | 10/2017 |
|---|---|---|
| KR | 10-1794930 B1 | 11/2017 |
| KR | 10-2018-0088476 A | 8/2018 |
| KR | 10-1913774 B1 | 10/2018 |
| KR | 10-1978700 B1 | 5/2019 |
| KR | 10-2020-0051151 A | 5/2020 |

OTHER PUBLICATIONS

Office Action for KR 10-2020-0058944 by Korean Intellectual Property Office dated Mar. 12, 2025.

\* cited by examiner

LIFTING BAND

CROSS-REFERENCE TO RELATED APPLICATIONS

This application is a National Phase Entry Application of PCT Application No. PCT/KR2021/005963 filed on May 12, 2021, which claims priority to Korean Patent Application No. 10-2020-0058944 filed on May 18, 2020, in Korean Intellectual Property Office, the entire contents of which are hereby incorporated by reference in its entirety.

TECHNICAL FIELD

The present invention relates to a lifting band.

BACKGROUND ART

Recently, in order to beautifully keep an appearance, there has been an increasing demand for give elasticity to skin through massage or acupressure or for correcting a chin line to a V-line. As part of this, a lifting band for correcting a chin line by pressing a face is widely used.

In general, a lifting band is for correcting a line beautifully. The lifting band may correct a chin line by pressing flesh around a chin. Both end portions of the lifting band are fixedly hooked on ears to press the fresh around the chin.

However, there is a problem in that the conventional lifting band can only correct a line by simply pressing flesh of a user but cannot achieve other effects such as skin improvement.

DISCLOSURE

Technical Problem

The present invention is directed to providing a lifting band capable of not only pressing flesh of a user to correct a line and but also implementing a skin improving effect using light.

The present invention is also directed to providing a lifting band capable of providing heat to skin of a user as well as light for improving the skin of the user.

Technical Solution

One aspect of the present invention provides a lifting band including: a band member provided in a plate shape having stretchability and elasticity and having a predetermined area; at least one light source part disposed on one surface of the band member and including a plurality of light-emitting diodes (LEDs) configured to, when power is applied, emit light having a certain wavelength band to improve skin, and a cap member fixed to one surface of the band member to cover the at least one light source part.

The light source part may include a support member having a plate shape, a certain area, and pliability and an insulating property, a plurality of circuit patterns which are not electrically connected to each other, are formed in a plane shape having a certain area, and are attached to one surface of the support member, the plurality of LEDs mounted on the plurality of circuit patterns to electrically connect two adjacent circuit patterns, and a cover member configured to cover one surface of the support member to cover the plurality of circuit patterns and the plurality of LEDs.

The circuit pattern may be formed of a conductive microfiber web in which a conductive material is plated on a microfiber web.

The light source part may include a support member having a plate shape, a certain area, a pliability, and an insulating property, a porous substrate stacked on one surface of the support member, a plurality of circuit patterns which are not electrically connected to each other, are formed on the porous substrate in a plane shape having a certain area, the plurality of LEDs mounted on the plurality of circuit patterns to electrically connect two adjacent circuit patterns, and a cover member configured to cover one surface of the support member to cover the circuit patterns and the plurality of LEDs, wherein each of the circuit patterns may include a first pattern formed as a printed pattern on the porous substrate such that a conductive material fills pores formed in the porous substrate, and a second pattern attached to one surface of the first pattern.

The second pattern may be formed of a conductive microfiber web in which a conductive material is plated on a microfiber web.

The cover member may include a plurality of convex portions protruding outward in a region corresponding respectively to the plurality of LEDs, each of the LEDs may be accommodated in one of inner spaces of the convex portion corresponding thereto, and the inner space of the convex portion may have a size that is larger than that of the LED.

Two circuit patterns to which power is applied among the plurality of circuit patterns may have a wider area than the other circuit patterns.

The cap member may include exposure holes formed to pass through regions corresponding respectively to the plurality of LEDs.

The lifting band may further include a heat generation part disposed between the light source part and the cap member to generate heat when power is applied.

The heat generation part may include a base substrate having a plate shape, lead electrode portions formed on one surface of the base substrate and including two lead electrodes not physically connected to each other, branch electrode portions including two branch electrodes which extend from the two lead electrodes such that the two branch electrodes are not electrically connected to each other and partial lengths thereof face each other, and conductive heat generation materials which have a certain area, are formed to be positioned at overlapping portions of the two branch electrodes facing each other, and when power is supplied, generate heat while electrically connect the two branch electrodes.

The heat generation part may include the plurality of branch electrode portions spaced apart from each other by a certain interval in a length direction of the lead electrode, and the plurality of conductive heat generation materials provided respectively on the plurality of branch electrode portions, and the plurality of branch electrode portions and the plurality of conductive heat generation materials may be disposed to be positioned at positions that do not overlap with the plurality of LEDs provided in the light source part.

The base substrate may include a film member having an insulating property, and a porous substrate stacked on one surface of the film member, and the lead electrode portion and the branch electrode portion may be formed on the porous substrate.

The lifting band may include a pair of magnetic terminals for an electrical connection with an external power supply.

Advantageous Effects

According to the present invention, various cosmetic effects can be obtained simultaneously by not only pressing flesh of a user to correct a line but also implementing a skin improving effect using light.

In addition, according to the present invention, by proving heat to skin of a user as well as light for improving the skin of the user, it is possible to promote the skin penetration of an active ingredient applied to the skin of the user.

Figure 1:
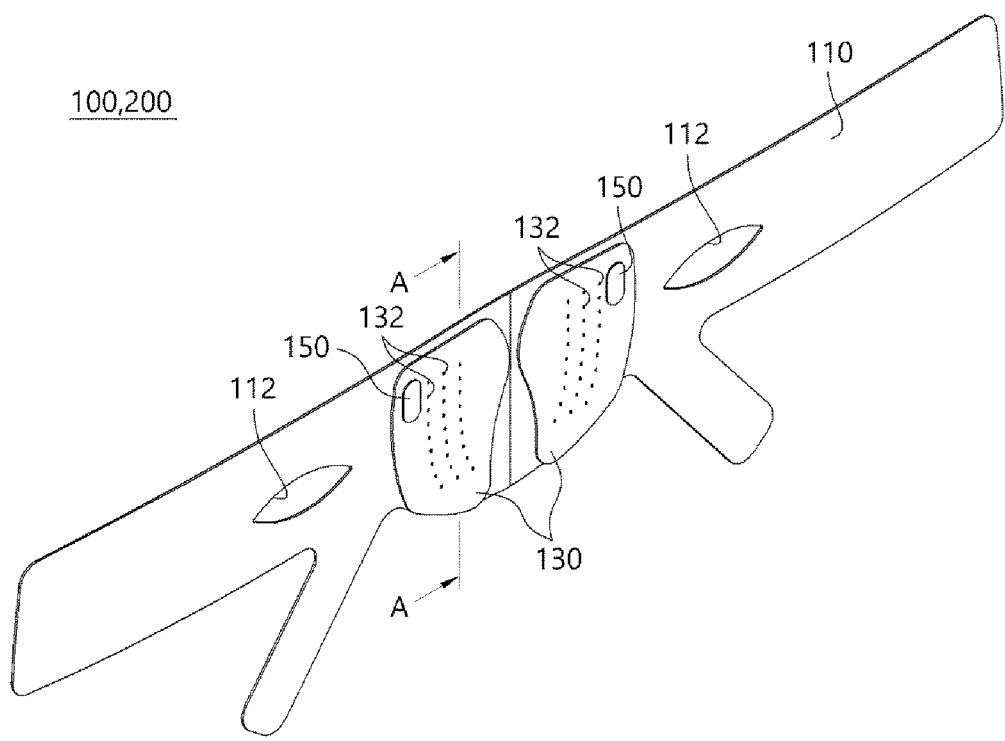
FIG. 1 is a view illustrating a lifting band according to one embodiment of the present invention.

| 100, 200: lifting band | 110: bend member |
| 120, 220: light source part | 130: cap member |
| 140: heat generation part | 150: electrode terminal |
| 160, 260, 360: fixing portion | 170: connection cable |

MODES OF THE INVENTION

Hereinafter, embodiments of the present invention will be described in detail with reference to the accompanying drawings so as to be easily practiced by a person of ordinary skill in the art to which the present invention pertains It should be understood that the present invention may be embodied in various different forms and is not limited to the following embodiments. Parts irrelevant to description are omitted in the drawings in order to clearly describe the present invention, and like reference numerals refer to like elements throughout the specification.

Figure 2:
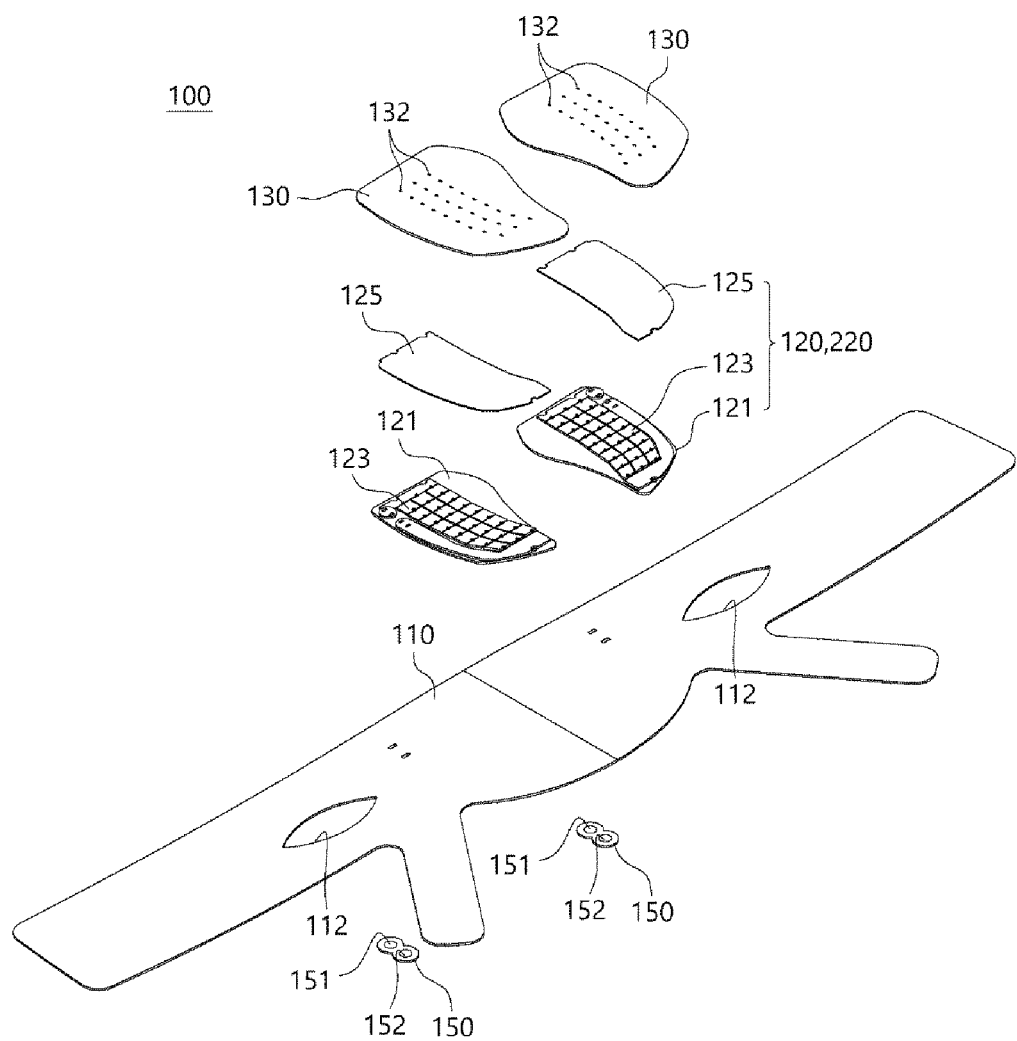
FIG. 2 is an exploded view illustrating a detailed configuration applicable to FIG. 1.
Figure 8:
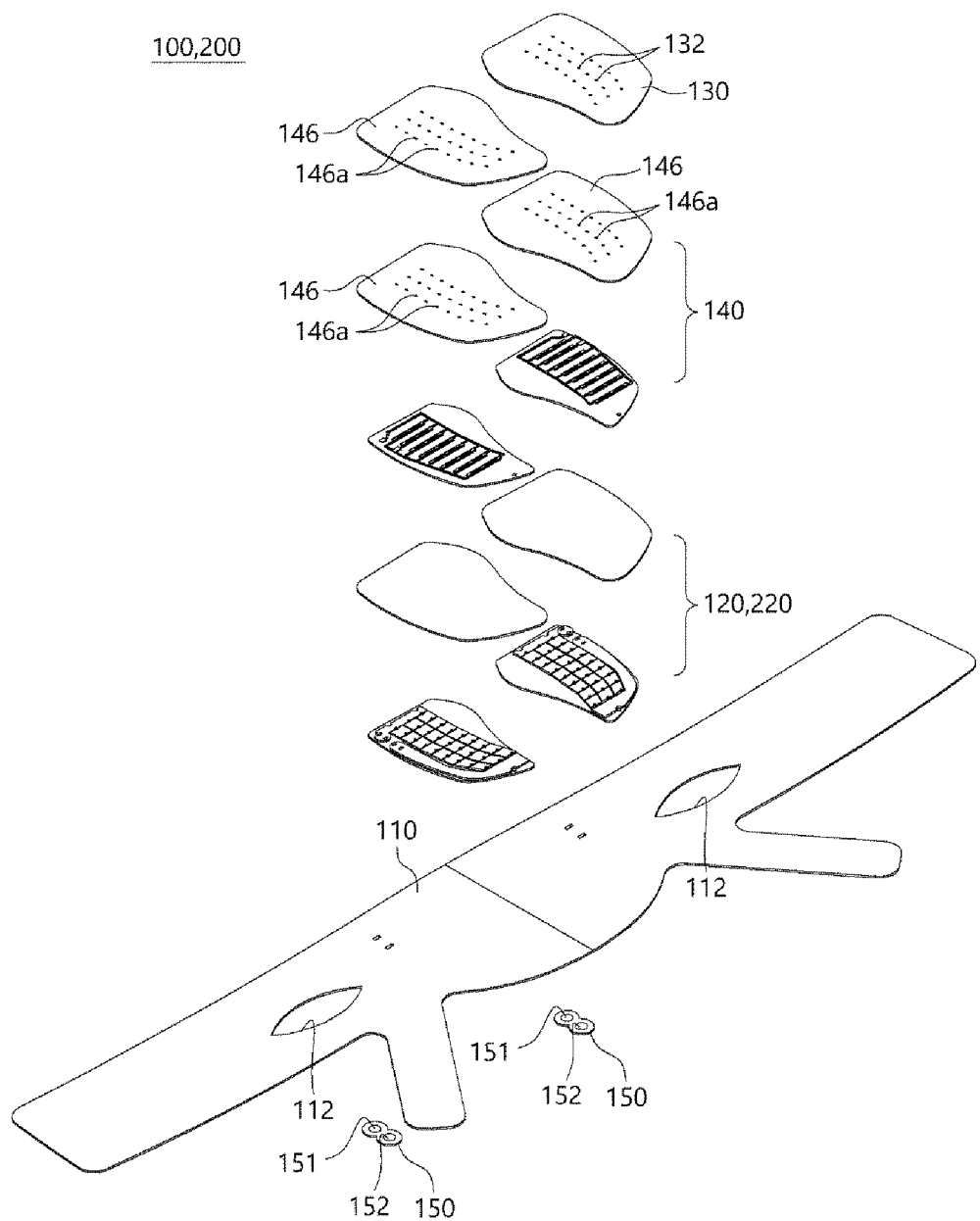
FIG. 8 is an exploded view illustrating another type of a detailed configuration applicable to FIG. 1.

As shown in FIGS. 1, 2, and 8, a lifting band 100 or 200 according to one embodiment of the present invention includes a band member 110, a light source part 120 or 220, and a cap member 130.

The band member 110 may be provided in a plate shape having a certain area so as to cover a chin line of a user, and both end portions thereof may be fixed.

In addition, the band member 110 may be made of a material having stretchbility and elasticity to pull and press skin of a user and may be made of a biocompatible material.

As an example, the band member 110 may be provided to have an area sufficient to cover a chin of a user and a front part of a neck. In a state in which the band member 110 covers the chin of the user and the front part of the neck, both end portions of the band member 110 may be coupled to each other directly or through a separate member. In addition, as a material of the band member 110, a cloth, a fabric, a non-woven fabric, leather, silicone, a polymer film such polyurethane, rubber, or the like may be used.

Thus, when the band member 110 is fixed to a face of a user to cover a chin of the user and a front part of a neck, the band member 110 may pull and press skin of the user.

Accordingly, by using a pressing force provided from the band member 110, the user can obtain cosmetic effects such as an effect of correcting a chin line, an effect of improving a nasolabial fold, and an improving of lifting a neck part.

Here, the band member 110 may include at least two opening holes 112 that are formed to pass through the band member 110 such that ears of a user are exposed to the outside in a state in which the band member 110 is fixed to a face of the user.

Figure 14:
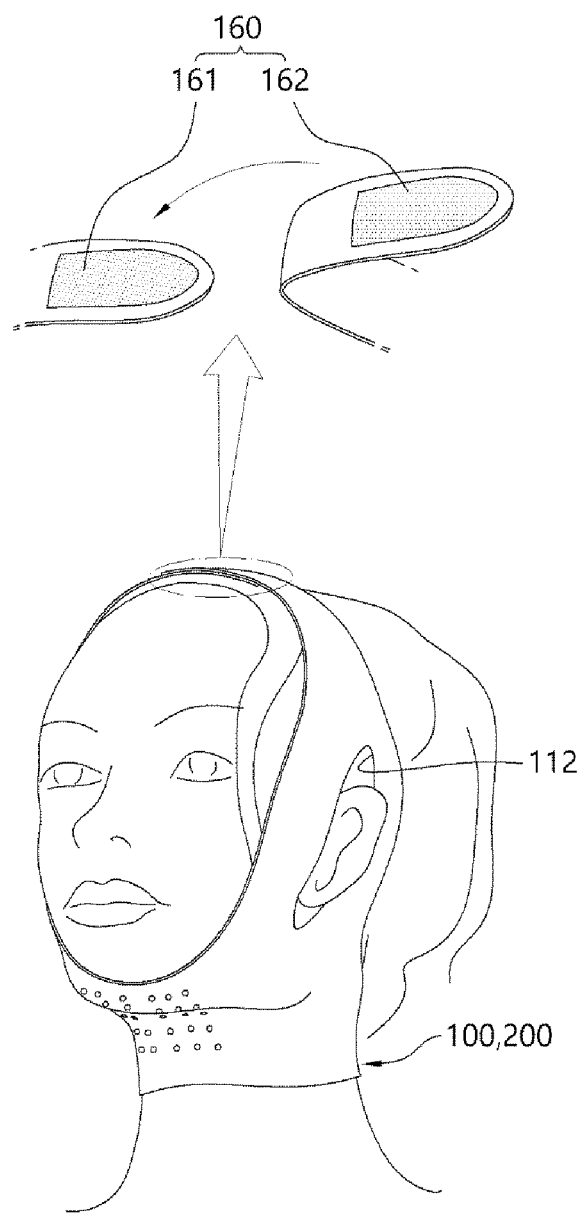
FIGS. 14 to 16 are views illustrating various types of coupling portions applicable to the lifting band according to the present invention.
Figure 15:
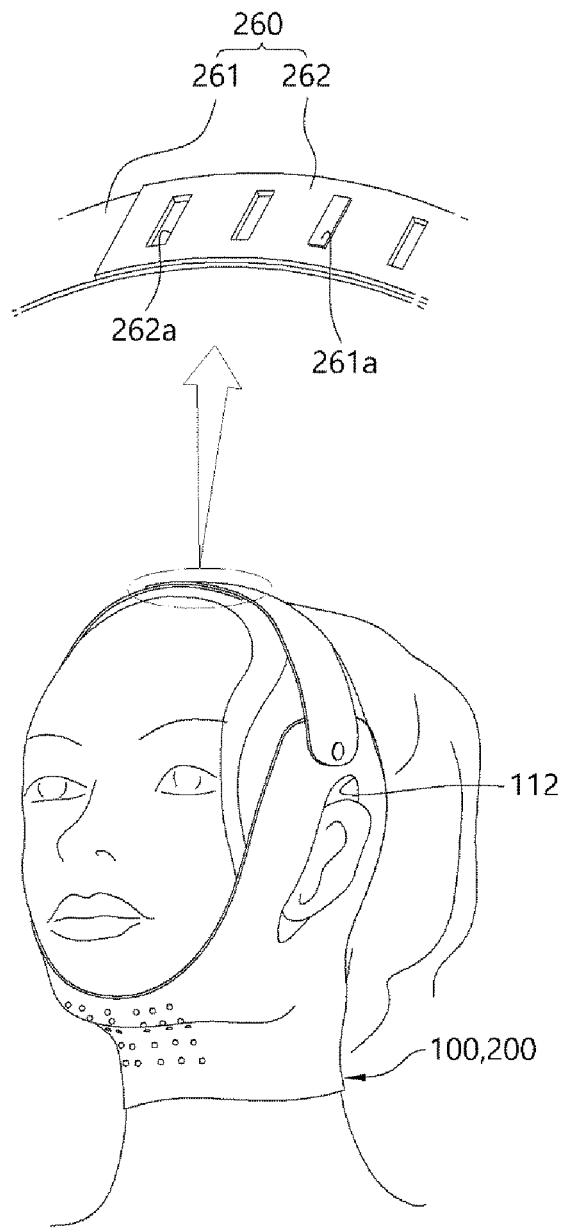
Figure 16:
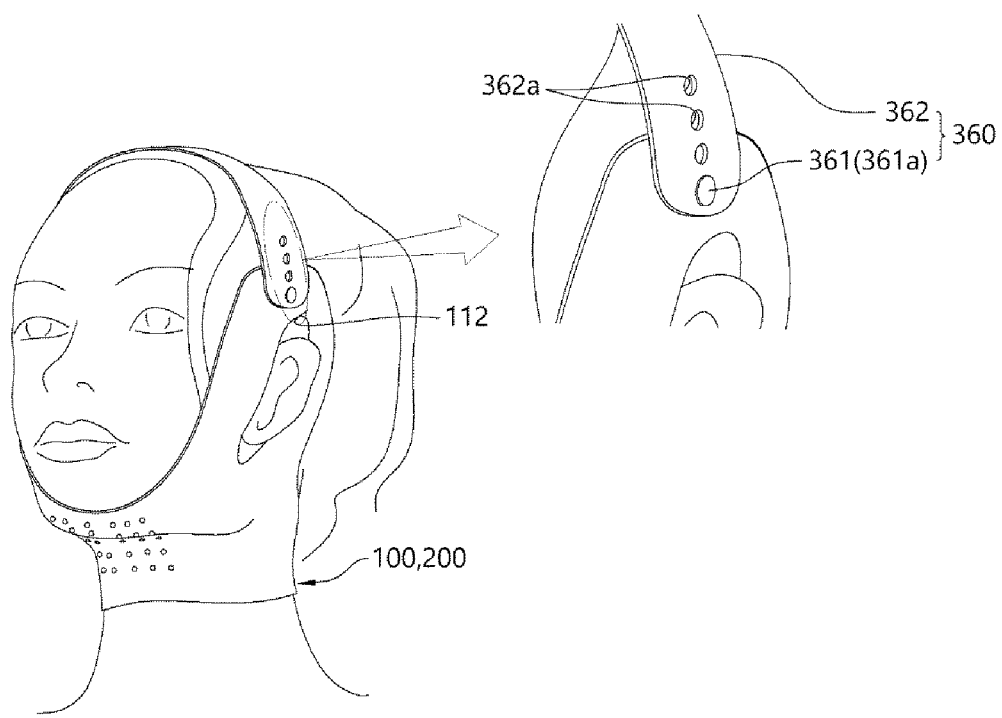

Accordingly, as shown in FIGS. 14 to 16, when the band member 110 is worn on the face of the user, the band member 110 may cover a chin of the user and a front part of a neck, and both ears of the user may be disposed in the two opening holes 112.

As a result, in a state in which the user wears the lifting band 100 or 200 according to one embodiment of the present invention on the face, even when the band member 110 pulls and presses a facial skin of the user through stretchability and elasticity, ears of the user may remain exposed to the outside through the two opening holes 112.

The light source part 120 or 220 may be disposed on one surface of the band member 110 and may emit light having a certain wavelength band when power is applied.

As an example, one light source part 120 or 220 may be provided, and a plurality of light source parts 120 or 220 may also be disposed on one surface of the band member 110 to be spaced apart from each other by a certain interval.

Thus, by using the lifting band 100 or 200 according to one embodiment of the present invention, a user can obtain cosmetic effects such as a chine line correcting effect, a nasolabial fold improving effect, and a neck part lifting and improving effect using a pressing force provided from the band member 110 as well as a skin improving effect using light provided from the light source part 120 or 220.

As an example, the skin improving effect may be a skin soothing effect, an skin texture improving effect, a sensitive skin caring and soothing effect, a skin contour improving effect, a skin elasticity improving effect, a skin elasticity restoring effect, a skin lifting effect, a skin gloss improving effect, or the like.

Figure 3:
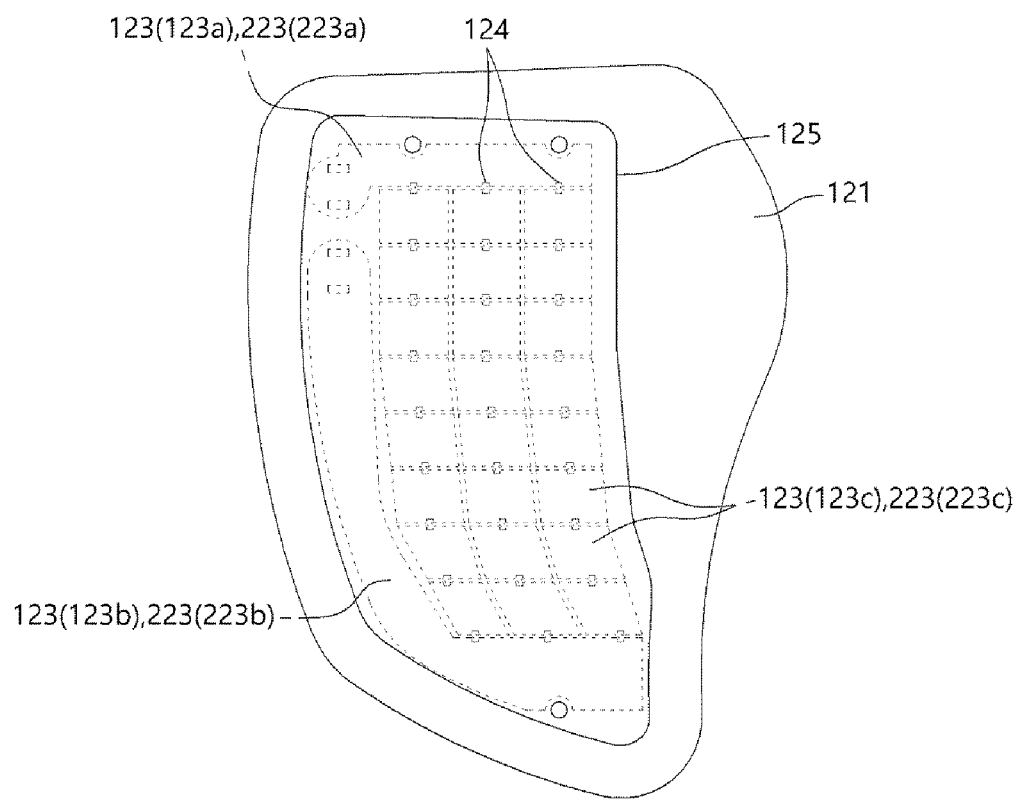
FIG. 3 is a plan view illustrating a light source part in FIG. 2.
Figure 4:
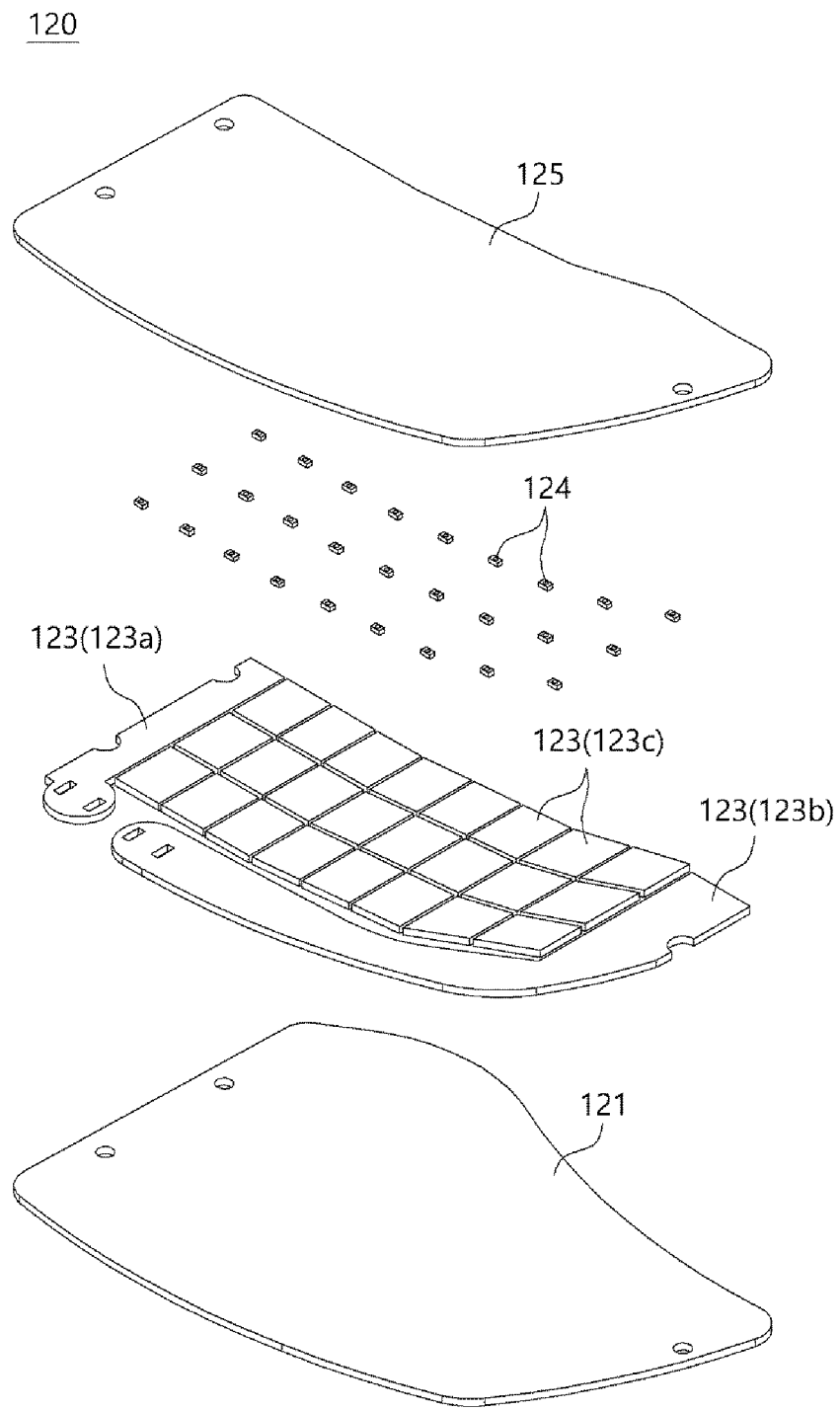
FIG. 4 is an exploded view illustrating a light source part applicable to FIG. 3.
Figure 5:
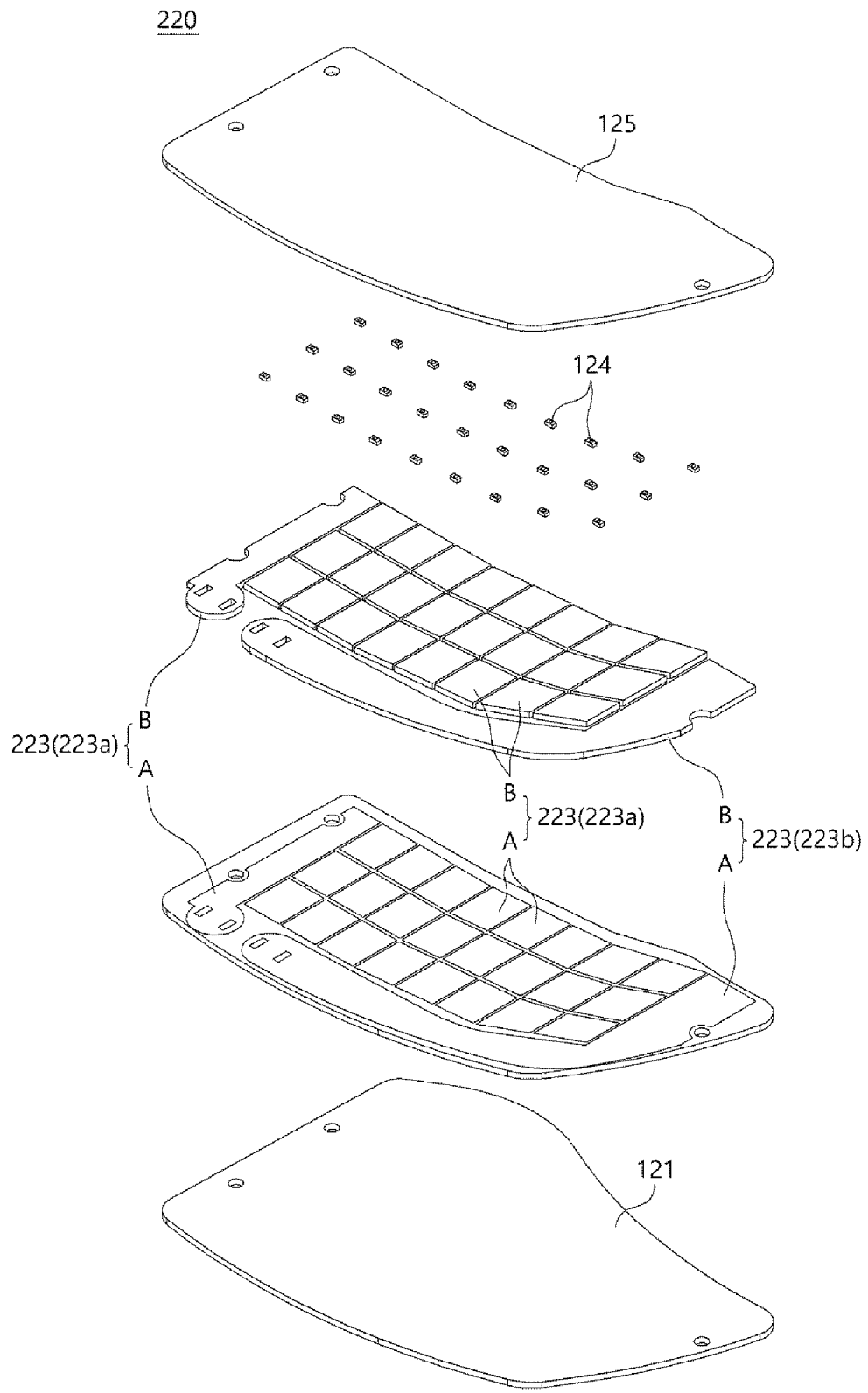
FIG. 5 is an exploded view illustrating another type of a light source part applicable to FIG. 3.

To this end, as shown in FIGS. 3 to 5, the light source part 120 or 220 may include a support member 121, a plurality of circuit patterns 123 or 223, a plurality of light-emitting diodes (LEDs) 124, and a cover member 125.

Specifically, the support member 121 may be a plate-shaped member having a certain area, and the plurality of circuit patterns 123 or 223 may be formed on one surface of the support member 121 without being electrically connected to each other.

In addition, the plurality of LEDs 124 may be mounted on one surface of the support member 121 to electrically connect two adjacent circuit patterns 123 or 223 to each other, and the cover member 125 may cover the one surface of the support member 121 to cover the plurality of circuit patterns 123 or 223 and the plurality of LEDs 124.

Here, each of the support member 121 and the cover member 125 may be made of a material having pliability and an insulating property. As an example, each of the support member 121 and the cover member 125 may be a polyurethane (PU) film, but a material of the support member 121 and the cover member 125 is not limited thereto. Any material having pliability and an insulating property may be used without limitation.

Thus, the plurality of LEDs 124 may be arranged on one surface of the support member 121 in a certain pattern, and may electrically connect to each other the plurality of circuit patterns 123 or 223.

Accordingly, the light source part 120 or 220 may form a surface light source through the plurality of LEDs 124 arranged on one surface of the support member 121, and the lifting band 100 or 200 according to one embodiment of the present invention may radiate light generated in the form of a surface light source from the light source part 120 or 220 onto a large area of skin of a user.

In this case, the plurality of circuit patterns 123 or 223 may be formed in a linear shape and may also be formed in a planar shape having a certain area to secure processing ease, secure conduction stability, and reduce an amount of heat generation.

In addition, among a plurality of circuit patterns 123*a*, 123*b*, and 123*c*, or 223*a*, 223*b*, and 223*c*, two circuit patterns 123*a* and 123*b* or 223*a* and 223*b* to which power is applied are provided to have an area that is wider than that of the remaining circuit patterns 123*c* or 223*c*. The two circuit patterns 123*a* and 123*b* or 223*a* and 223*b* may be connected in parallel with some circuit patterns 123*c* or 223*c* among the remaining circuit patterns 123*c* or 223*c* through the LEDs 124. Among the remaining circuit patterns 123*c* or 223*c*, some circuit patterns 123*c* or 223*c* may be provided in plural.

Accordingly, power applied through the two circuit patterns 123*a* and 123*b* or 223*a* and 223*b* may be transmitted through a plurality paths via the plurality of circuit patterns 123*c* or 223*c* connected in parallel with the two circuit patterns 123*a* and 123*b* or 223*a* and 223*b*, thereby shortening a path of a current applied to each LED 124.

As a result, even when the plurality of LEDs 124 are mounted on the plurality of circuit patterns 123*a*, 123*b*, and 123*c* or 223*a*, 223*b*, and 223*c*, a total supply time of power supplied to each LED 124 may be shortened to shorten a reaction time of the light source part 120 or 220 and considerably reduce a magnitude of a driving voltage required to allow the light source part 120 or 220 to emit heat.

Meanwhile, each of the plurality of circuit patterns 123 may be formed of a conductive microfiber web in which a conductive material E is plated on a microfiber web formed in which microfibers F have pores D. As shown in FIG. 4, each of the plurality of circuit patterns 123 may be attached directly to one surface of the support member 121.

Figure 11:
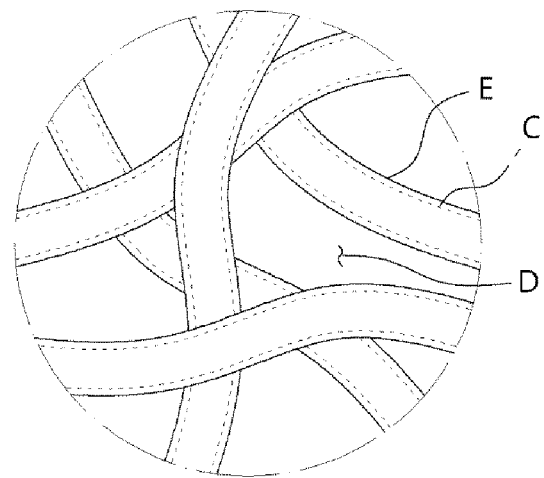
FIG. 11 is a schematic view illustrating a circuit pattern applicable to the lifting band according to the present invention.

That is, as shown in FIG. 11, the circuit pattern 123 may be formed by processing the conductive microfiber web, in which the conductive material E is plated to surround surfaces of the microfibers F constituting the microfiber web, into a certain shape. The circuit pattern 123 may be attached directly to one surface of the support member 121 through an adhesive.

Accordingly, the circuit pattern 123 may have flexibility like the support member 121. When the LED 124 is mounted on the circuit pattern 123 using a solder paste, the solder paste may permeate into the pores D formed in the conductive microfiber web.

As a result, the LED 124 mounted on the circuit pattern 123 may be strongly coupled to the circuit pattern 123 to be stably driven even when the support member 121 is folded or crumpled.

As another example, each of the plurality of circuit patterns 223 may be formed as at least two layers as shown in FIG. 5. That is, each circuit pattern 223 may be configured to maintain conduction stability even when the support member 121 is crumpled or bent.

To this end, the light source part 220 may further include a first porous substrate 222 stacked on one surface of the support member 121, and the circuit pattern 223 may include a first pattern A formed directly on the first porous substrate 222 and a second pattern B attached to one surface of the first pattern A.

In this case, the LED 124 may be mounted on one surface of the second pattern B through a solder paste.

Here, the first porous substrate 222 may have pores having a certain size, and a material of the first porous substrate 222 may be a cloth, a fabric, a nonwoven fabric, a porous film, a membrane, or the like. However, the first porous substrate is not limited to the above-described material, and any material having pores with a certain size and having stretchability and flexibility may be used without limitation.

Figure 12:
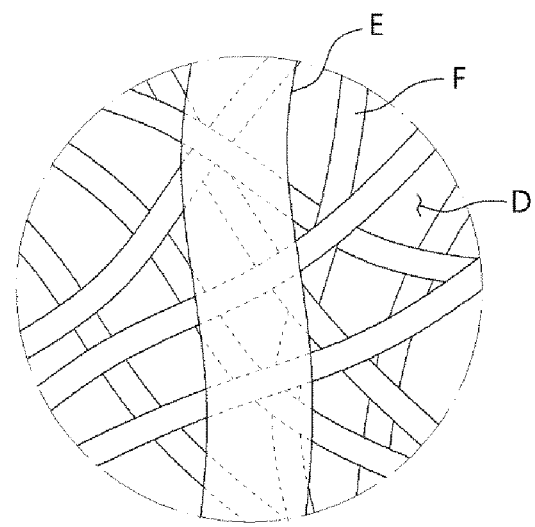
FIG. 12 is a schematic view illustrating another type of a circuit pattern applicable to the lifting band according to the present invention.

As a specific example, as shown in FIG. 12, the first porous substrate 222 may be formed of a nanofiber web in which nanofibers C including a synthetic polymer are accumulated in a three-dimensional network structure to have the pores D.

As a non-limiting example, the first porous substrate 222 may be formed of a single-layered or multi-layered nanofiber web accumulated to have the pores D by electrospinning a spinning solution in which a synthetic polymer and a solvent are mixed. Here, the solvent may be water or alcohol. Other than water or alcohol, the solvent may be provided in a form in which an organic solvent such as dimethylacetamide or acetone is used alone or the organic solvents are mixed with each other.

In this case, the synthetic polymer may be a fiber moldability polymer capable of implementing a nanofiber web having flexibility and stretchability through electrospinning. As a specific example, polyvinylidene fluoride (PVDF) may be used alone as the synthetic polymer, but the synthetic polymer may be formed by mixing PVDF and polyethersulfone (PES) in a certain ratio so as to secure heat resistance against a high temperature when the LED 124 is soldered.

However, a material of the synthetic polymer is not limited thereto, and any fiber moldability polymer which is capable of implementing a nanofiber web through electrospinning and has flexibility and elasticity, may be used without limitation.

In this case, the first pattern A may be formed directly on the first porous substrate 222, and the second pattern B may be attached to one surface of the first pattern A. Accordingly, the first porous substrate 222 may serve as a circuit board on which electronic components such as the LED 124 may be mounted.

That is, as shown in FIG. 12, the first pattern A may be a printed pattern formed directly on the first porous substrate 222 such that a conductive material fills the pores D formed in the first porous substrate 222.

As an example, the first pattern A may be a printed pattern formed directly on the first porous substrate 222 through a printing method using a conductive paste, and the conductive paste may completely or partially fill the pores D formed in the first porous substrate 222 in addition to a surface of the first porous substrate 222. Here, the conductive paste may be a silver (Ag) paste but is not limited thereto, and any known conductive paste may be applied.

In addition, the second pattern B may be formed of a conductive microfiber web in which the conductive material E is plated on a microfiber web in which the microfibers F have the pores D.

Like the circuit pattern 123 of the above-described embodiment, as shown in FIG. 11, the second pattern B may be formed by processing the conductive microfiber web, in which the conductive material E is plated to surround a surface of the microfibers F constituting the microfiber web, into a certain shape. The second pattern B may be attached to one surface of the first pattern A through an adhesive.

Accordingly, the second pattern B may have stretchability and flexibility like the first porous substrate 222. When the first porous substrate 222 is stretched or contracted by an external force, the second pattern B may be stretched or contracted like the first porous substrate 222.

In this case, the second pattern B may be formed by punching the conductive microfiber web, in which the conductive material E is plated to surround the surfaces of the microfibers F constituting the microfiber web, to have the same shape as the first pattern A formed directly on the first porous substrate 222.

Such a second pattern B may be attached to one surface of the first pattern A through a conductive adhesive layer. Here, the conductive adhesive layer may be an adhesive layer including a vertical conductive filler such as nickel (Ni).

Accordingly, the first pattern A and the second pattern B may have the same pattern shape and may be electrically connected to each other through the conductive adhesive layer.

As such, the lifting band 200 according to one embodiment of the present invention includes the first pattern A and the second pattern B which are formed in different ways, and The second pattern B is stacked on one surface of the first pattern A to form the circuit pattern 223, thereby improving the conduction stability of the circuit pattern 223.

That is, when the first porous substrate 222 having stretchability and flexibility is stretched or contracted during use, since the first pattern A and the second pattern B formed in different ways mutually compensate for a short circuit, the LED 124 can be stably operated.

Meanwhile, an average pore size of the microfiber web constituting the second pattern B may be greater than an average pore size of the first porous substrate 222.

Thus, when the LED 124 is mounted on one surface of the second pattern B, a solder paste for mounting the LED 124 may sufficiently permeate into the pores D of the conductive microfiber web constituting the second pattern B and may be prevented from permeating into the pores D of the first porous substrate 222 on which the first pattern A is formed.

As a result, the LED 124 mounted on the second pattern B may form a strong bond with the second pattern B through the solder paste.

When power is supplied, the LED 124 may generate light having a certain wavelength band.

The plurality of LEDs 124 may be provided and may be mounted on one surface of the circuit pattern 123 or 223 to connect two adjacent circuit patterns 123 and 223 as described above.

Accordingly, the lifting band 100 or 200 according to one embodiment of the present invention can implement a surface light source through the plurality of LEDs 124, thereby radiating light onto a large area of skin of a user.

In this case, the LED 124 may emit light having one wavelength band. For example, the LED 124 can destroy bacteria and treat acne by emitting light in a band of 405 nm to 420 nm that can be absorbed by epithelial tissue of skin.

However, a wavelength band of the LED 124 is not limited thereto, and the LED 124 may radiate light having any wavelength band suitable for a targeted skin improving effect in a band of 405 nm to 970 nm.

In addition, the LED 124 may radiate light in one wavelength band but may be provided to radiate light having different wavelength bands. As a non-limiting example, as the LEDs 124, a plurality of light-emitting element, which radiate light having different wavelength bands, may be integrally formed. Alternatively, the LEDs 124 may be provided as a plurality of LEDs, and the plurality of LEDs may be provided as two or more LEDs for radiating light having different wavelength bands.

As described above, the cover member 125 may be provided on one surface of the support member 121 to cover the plurality of circuit patterns 123 or 223 and the plurality of LEDs 124.

Thus, the cover member 125 can prevent the circuit patterns 123 or 223 and the LEDs 124 from being exposed to the outside and may block foreign materials from being introduced into the circuit patterns 123 or 223 and the LEDs 124.

In addition, the cover member 125 may be made of a material having flexibility and pliability as described above and may be made of a material having not only flexibility and pliability but also a moisture-proof property to block the movement of moisture.

In addition, the cover member 125 may be made of a light-transmitting material to smoothly transmit light emitted from the LED 124.

Figure 6:
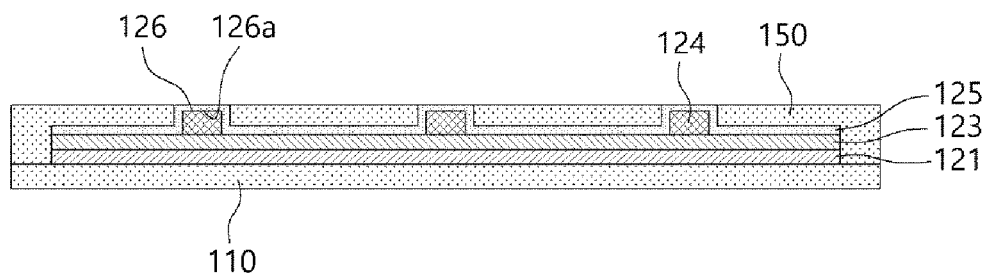
FIG. 6 is a cross-sectional view in direction A-A of FIG. 1.
Figure 7:
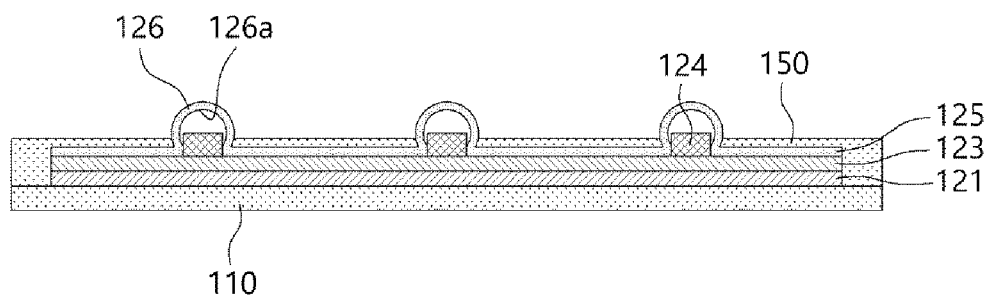
FIG. 7 is a view illustrating a modified example of FIG. 6.

In this case, as shown in FIGS. 6 and 7, the cover member 125 may include a plurality of convex portions 126 protruding outward in a region corresponding to the plurality of LEDs 124 mounted on one surface of the circuit pattern 123 or 223.

In this case, the cap member 130 may include exposure holes 132 formed to pass through regions corresponding to the plurality of convex portions 126.

Accordingly, the plurality of LEDs 124 may be accommodated in inner spaces 126a of the convex portions 126 corresponding thereto. In a state of being accommodated in the inner space 126a of the convex portion 126, each of the LEDs 124 may be exposed to the outside of the cap member 130 through the exposure hole 132.

As a result, light generated from the LED 124 may be smoothly radiated onto skin of a user without being blocked by the cap member 130.

In this case, as shown in FIG. 6, the inner space 126a of the convex portion 126 may be provided to have substantially the same size as the LED 124.

In this case, an inner surface of the convex portion 126 may be in contact with a surface of the LED 124, and an exposed surface of the convex portion 126 may form the same surface as the exposed surface of the cap member 130 and may be positioned in the exposure hole 132. That is, the exposed surface of the convex portion 126 may be disposed to not protrude outward from an exposed surface of the cap member 130.

Accordingly, in a process of using the lifting band 100 or 200 according to one embodiment of the present invention, it is possible to prevent foreign materials attached on skin from being introduced into the exposure hole 132 to be caught in the exposure hole 132.

As another example, the inner space 126a of the convex portion 126 may be provided to have a size that is larger than that of the LED 124 as shown in FIG. 7.

In this case, the convex portion 126 may completely fill the exposure hole 132, and the exposed surface of the convex portion 126 may be formed to protrude from the exposed surface of the cap member 130 by a certain height.

Accordingly, the inner space 126a of the convex portion 126 may include a space in which the LED 124 is disposed and a space in which the LED 124 is not disposed, and an embossing effect may be implemented through the space in which the LED 124 is not disposed.

Thus, in a process of using the lifting band 100 or 200 according to one embodiment of the present invention, it is possible to fundamentally block foreign materials attached to skin from being introduced into the exposure hole 132. In addition, since the exposed surface of the convex portion 126 is formed to protrude from the exposed surface of the cap member 130 by a certain height, even though the convex portion 126 comes into direct contact with skin of a user, a shape of the convex portion 126 may be deformed through the space in which the LED 124 is not disposed, thereby to preventing the user from feeling uncomfortable.

The cap member 130 may be fixed to one surface of the band member 110 so as to cover the light source part 120 or 220.

In this case, as described above, the cap member 130 may include the plurality of exposure holes 132 formed to pass through regions corresponding to the plurality of LEDs 124. Thus, each LED 124 may be disposed in the exposure hole 132, and light generated from the LED 124 may be emitted to the outside through the exposure hole 132.

Like the band member 110, such a cap member 130 may be made of a material having stretchability and elasticity so as to pull and press skin of a user and may be made of a biocompatible material.

As an example, as a material of the cap member 130, a cloth, a fabric, a non-woven fabric, leather, silicone, a polymer film such polyurethane, rubber, or the like may be used.

Here, the cap member 130 may be made of the same material as the band member 110 or may be made of a different material from the band member 110.

Figure 9:
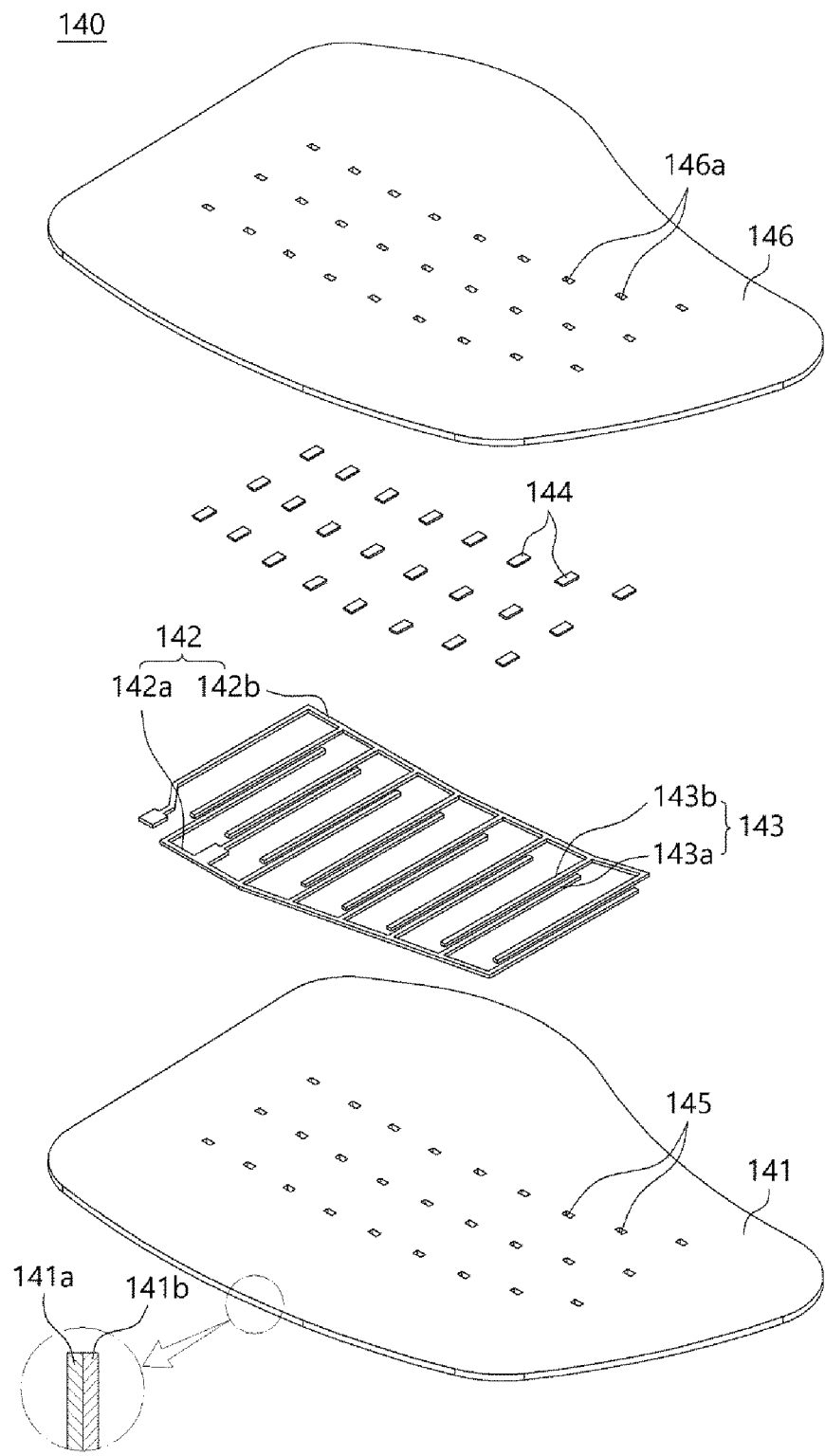
FIG. 9 is an exploded view illustrating a detailed configuration of a heat generation part applicable to FIG. 8.
Figure 10:
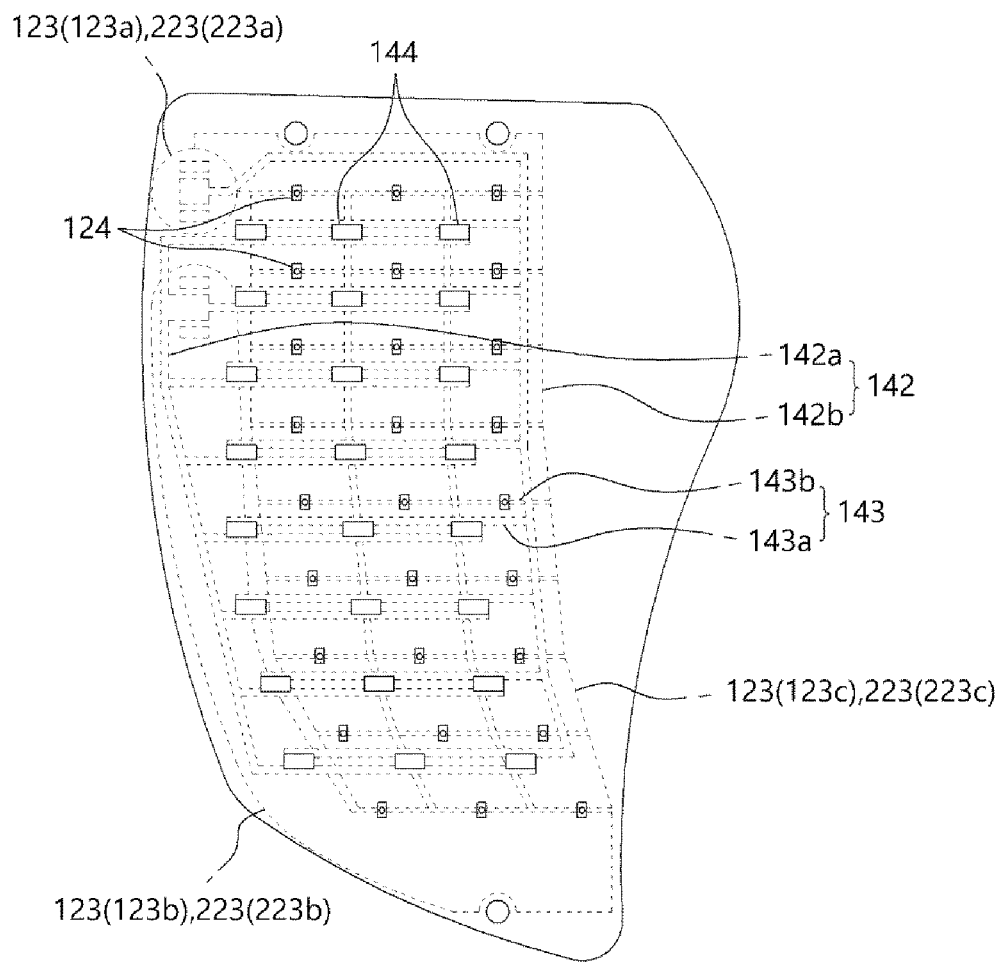
FIG. 10 is a plan view illustrating a state in which the heat generation part and the light source part overlap each other and which is applicable to FIG. 8.

Meanwhile, as shown in FIGS. 8 to 10, the lifting band 200 according to one embodiment of the present invention may further include a heat generation part 140 for implementing a heating function.

As an example, the heat generation part 140 may be disposed to be positioned between the light source part 120 or 220 and the cap member 130.

Such a heat generation part 140 may generate and provide heat to skin of a user to promote skin penetration of an active ingredient applied on the skin of the user or may transmit heat to the skin of the user to assist in activating collagen and open pores to induce the discharge of unnecessary wastes or the like.

Accordingly, the lifting band 200 according to one embodiment of the present invention can implement all of a face line correcting effect using a pressing force of the band member 110, a skin improving effect using light of the light source part 120 or 220, and a skin improving effect using heat of the heat generation part 140.

In the lifting band 200 according to the present embodiment, as the light source part 120 or 220, light source parts shown in FIGS. 4 and 5 may be selectively applied.

In this case, the heat generation part 140 may be implemented to generate heat at a constant temperature irrespective of portions of the heat generation part.

To this end, as shown in FIG. 9, the heat generation part 140 may include a base substrate 141, a lead electrode portion 142, a branch electrode portion 143, and a conductive heat generation material 144.

The base substrate 141 may be provided in the form of a plate having a certain area.

Such a base substrate 141 may support the lead electrode portion 142 and the branch electrode portion 143 formed on at least one surface thereof and may block the lead electrode portion 142 and the branch electrode portion 143 from being electrically connected to the light source part 120 or 220.

In addition, the base substrate 141 may be made of a material having flexibility and pliability. Accordingly, even when the base substrate 141 is crumpled or bent due to an external force, it is possible to prevent cracks from being generated in the lead electrode portion 142 and the branch electrode portion 143.

To this end, as shown in FIG. 9, the base substrate 141 may include a film member 141a having an insulating property and a second porous substrate 141b stacked on one surface of the film member 141a.

As an example, the film member 141a may be made of a polymer resin having an insulating property and flexibility, such as PU, polyethylene terephthalate (PET), polypropylene (PP), polyethylene (PE), or PVDF. The second porous substrate 141b may be made of a cloth, a fabric, a non-woven fabric, a porous film, a membrane, or the like.

As a specific example, the film member 141a may be a PU film, and the base substrate 141 may be formed of a nanofiber web in which nanofibers including a synthetic polymer are accumulated in a three-dimensional network structure to have pores.

In this case, when the lead electrode portion 142 and the branch electrode portion 143 are formed on the second porous substrate 141b through a printing method using a conductive paste, the conductive paste may fill the pores. Accordingly, the base substrate 141 may serve as a circuit board on which the lead electrode portion 142 and the branch electrode portion 143 are patterned through the second porous substrate 141b.

As a non-limiting example, the second porous substrate 141b may be formed of a single-layered or multi-layered nanofiber web accumulated to have pores by electrospinning a spinning solution in which a synthetic polymer and a solvent are mixed.

Accordingly, the second porous substrate 141b is implemented in the form of a nanofiber web through a synthetic polymer having stretchability and pliability, thereby securing stretchability and pliability.

The lead electrode portion 142 and the branch electrode portion 143 may be formed in a certain pattern on at least one surface of the second porous substrate 141b as described above and may provide a conduction path through which a current flows when power is applied.

The lead electrode portion 142 and the branch electrode portion 143 may be formed in a certain pattern on one surface of the second porous substrate 141b through various known methods such as plating, etching, and printing methods using a conductive material.

As an example, the lead electrode portion 142 and the branch electrode portion 143 may be formed on the second porous substrate 141b through a printing method using a conductive paste. Here, the conductive paste may be an Ag paste but is not limited thereto, and any known conductive paste used to form an electrode may be used.

In this case, when power is applied, the lead electrode portion 142 and the branch electrode portion 143 may be electrically connected to each other through the conductive heat generation material 144.

As a specific example, as shown in FIG. 9, the lead electrode portion 142 may include two lead electrodes 142a and 142b which are formed on one surface of the base substrate 141 to be spaced apart from each other by a certain interval without being physically connected to each other.

Also, the branch electrode portion 143 may include two branch electrodes 143a and 143b which are respectively extend from the two lead electrodes 142a and 142b such that the electrodes 143a and 143b are not electrically connected to each other, and partial lengths thereof overlap each other.

That is, the lead electrode portion 142 may include a first lead electrode 142a and a second lead electrode 142b, the branch electrode portion 143 may include a first branch electrode 143a extending from the first lead electrode 142a and a second branch electrode 143b extending from the second lead electrode 142b, and the first branch electrode 143a and the second branch electrode 143b may be disposed such that portions of total lengths face each other.

In this case, the conductive heat generation material 144 may be formed on one surface of the base substrate 141 to cover an area of portions at which the first branch electrode 143a and the second branch electrode 143b face each other.

That is, the conductive heat generation material 144 may be formed to have an area including a partial or entire area of the portions at which the first branch electrode 143a and the second branch electrode 143b face each other.

Accordingly, the conductive heat generation material 144 may be formed to to fill the area of the portions facing each other between the first branch electrode 143a and the second branch electrode 143b while in direct contact with the first branch electrode 143a and the second branch electrode 143b.

In this case, a plurality of branch electrode portions 143 may be provided. The plurality of branch electrode portions 143 may be spaced apart from each other by a certain interval in a length direction of the lead electrode portion 142.

That is, each of a plurality of first branch electrodes 143a may extend from the first lead electrode 142a to be spaced apart from each other by a certain interval in a length direction of the first lead electrode 142a, and each of a plurality of second branch electrodes 143b may extend from the second lead electrode 142b to be spaced apart from each other by a certain interval in a length direction of the second lead electrode 142b.

In addition, the plurality of first branch electrodes 143a and the plurality of second branch electrodes 143b may be formed to be alternately arranged in the length direction of the lead electrode portion 142.

Accordingly, the plurality of branch electrode portions 143 may be spaced apart from each other by a certain interval in the length direction of the lead electrode portion 142.

In this case, a plurality of conductive heat generation materials 144 may also be provided. The plurality of conductive heat generation materials 144 may be formed on one surface of the base substrate 141 to connect two first and second branch electrodes 143a and 143b paired with each other.

Through this, when power is supplied, the conductive heat generation materials 144 may generate heat while electrically connect the first branch electrode 143a and the second branch electrode 143b which are paired with each other.

Accordingly, when power is supplied, the lifting band 200 according to the present embodiment may implement a heating function through heat generated by the heat generation part 140.

As a result, it is possible to promote the penetration of an active ingredient into skin of a user, thereby increasing an effect of enhancing skin care through the active ingredient. In addition, it is possible to transmit heat to skin of a user to assist in activating skin collagen and open pores to induce the discharge of unnecessary wastes or the like.

In this case, when the plurality of branch electrode portions 143 and the plurality of conductive heat generation materials 144 are provided, as shown in FIG. 10, the plurality of branch electrode portions 143 and the plurality of conductive heat generation materials 144 may be disposed to be positioned at positions that do not overlap with the LEDs 124.

Accordingly, even though the lifting band 100 or 200 according to one embodiment of the present invention includes both the light source part 120 or 220 and the heat generation part 140, the LED 124 and the conductive heat generation material 144 may be disposed at positions that do not overlap each other.

That is, the lifting band 100 or 200 according to one embodiment of the present invention may be disposed such that the LED 124 and the conductive heat generation material 144 which are heat sources do not overlap each other.

Accordingly, light generated from the LED 124 can be smoothly radiated onto skin of a user without being blocked by the conductive heat generation material 144, and the LED 124 can minimize heat generated from the conductive heat generation material 144 from being transmitted to the LED 124.

As a result, even though the lifting band 200 according to the present embodiment includes both the light source part 120 or 220 for a skin improving effect using light and the heat generation part 140 for a heating function, both the light source part 120 or 220 and the heat generation part 140 may smoothly operate.

In this case, the base substrate 141 may include arrangement holes 145 formed to pass through regions corresponding to the LEDs 124.

Accordingly, the LED 124 may be exposed to the outside through the arrangement hole 145 and the exposure hole 132 formed in the cap member 130.

Here, the heat generation part 140 may further include a plate-shaped cover sheet 146 disposed on one surface of the base substrate 141 so as to cover the lead electrode portion 142, the branch electrode portion 143, and the conductive heat generation material 144.

In this case, the cover sheet 146 may be made of a material having flexibility and pliability and may be made of a material having not only flexibility and pliability but also a moisture-proof property to block the movement of moisture.

In addition, the cover sheet 146 may include through-holes 146a formed to pass through regions corresponding to the arrangement holes 145.

Accordingly, even though the heat generation part 140 includes the cover sheet 146, the LED 124 may be exposed to the outside through the arrangement hole 145, the through-hole 146a, and the exposure hole 132 formed in the cap member 130.

Meanwhile, the conductive heat generation material 164 may be a conductive constant temperature heat generation material so as to uniformly generate heat to a target temperature when power is supplied. Here, the conductive constant temperature heat generation material may be a material of which, when a temperature rises, resistance is increased to suppress a heat-generating temperature. More specifically, the conductive constant temperature heat generation material may be a known (positive temperature coefficient) PTC material, more specifically, a conductive carbon paste.

As a result, when power is supplied and a heat-generating temperature of the heat generation part 140 reaches the target temperature, the conductive heat generation material 144 may block a flow of current through an increase in resistance to cut off an electrical connection between the first branch electrode 143a and the second branch electrode 143b, and when the heat-generating temperature of the conductive heat generation material 144 is less than the target temperature, the conductive heat generation material 144 may allow a current to flow through a decrease in resistance to electrically connect the first branch electrode 143a and the second branch electrode 143b to each other.

Accordingly, the heat generation part 140 may always generate heat at a uniform temperature through such a process.

Meanwhile, the lifting band 100 or 200 according to one embodiment of the present invention may use an embedded battery and may also receive driving power from the outside.

To this end, the lifting band 100 or 200 according to one embodiment of the present invention may include an electrode terminal 150 for applying power supplied from the outside.

A pair of electrode terminals 150 may be provided.

As an example, the electrode terminal 150 may include a first terminal 151 and a second terminal 152. Any one of the first terminal 151 and the second terminal 152 may be a positive electrode, and the other may be a negative electrode.

In this case, as described above, the first terminal 151 and the second terminal 152 may be provided on two circuit patterns 123 or 223 have an area that is wider than that of the remaining circuit patterns 123 or 223 among the plurality of circuit patterns 123 or 223 constituting the light source part 120 or 220. The first terminal 151 and the second terminal 152 may be provided to be exposed to the outside at one surface of the band member 110.

In addition, the first terminal 151 and the second terminal 152 may be magnetic terminals to increase use convenience of a user.

Accordingly, a user can connect an external power supply to the first terminal 151 and the second terminal 152 by using a magnetic force so that user convenience can be increased.

As an example, the lifting band 100 or 200 according to one embodiment of the present invention may be electrically connected to a separate power supply through a connection cable 170 having corresponding terminals 172 corresponding to the first terminal 151 and the second terminal 152. The corresponding terminals 172 may be provided as magnetic terminals like the first terminal 151 and the second terminal 152.

Accordingly, the lifting band 100 or 200 according to one embodiment of the present invention may be driven by receiving driving power from a power supply connected to the electrode terminal 150.

Meanwhile, the lifting band 100 or 200 according to one embodiment of the present invention may further include the connection cable 170 for an electrical connection with an external power source device that is a power supply.

Figure 13:
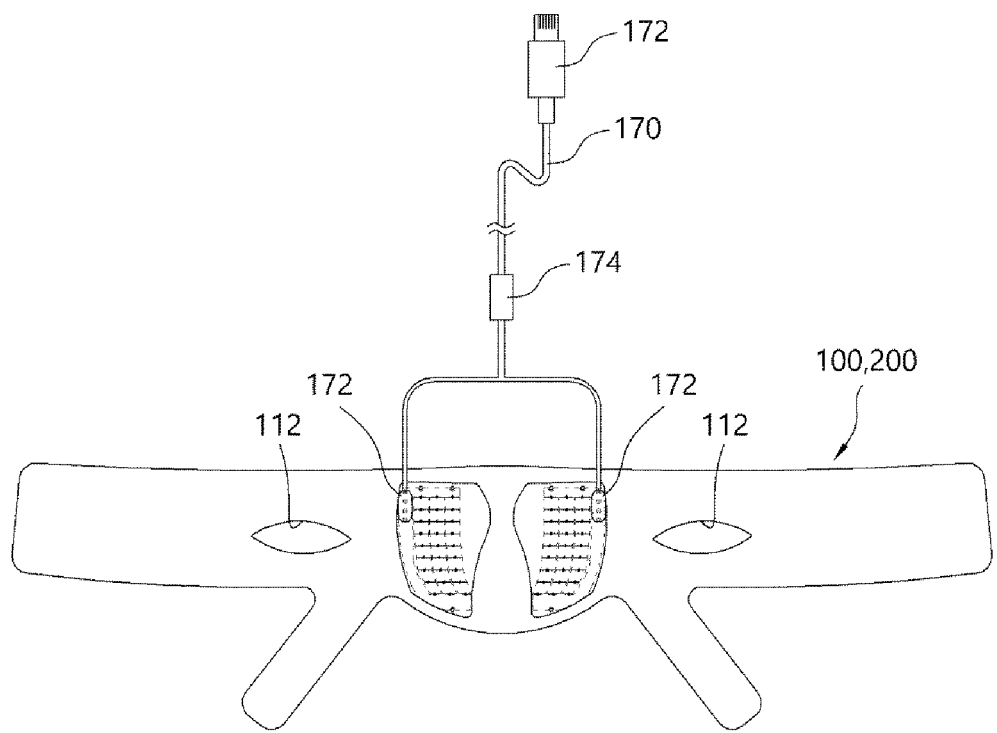
FIG. 13 is a view illustrating a state in which the lifting band and a connection cable are connected according to the present invention.

As shown in FIG. 13, the connection cable 170 may include a connected port 171 provided at one end portion thereof so as to be connected to an external power source device (not shown) and may include a corresponding terminal 172 provided at the other end portion thereof for an electrical connection with the electrode terminal 150.

Here, the external power source device may be a portable electronic device such as a mobile phone or an auxiliary battery.

Accordingly, the lifting band 100 or 200 according to one embodiment of the present invention may be driven using power provided from the external power supply device through the connection cable 170.

In this case, the connection cable 170 may further include a separate controller 174 for controlling the driving of the lifting band 100 or 200 according to one embodiment of the present invention. The controller 174 may be operated through manipulation of a user.

As an example, the controller 174 may control various functions of turning the light source part 120 or 220 on/off, selecting or changing a light emission mode of the light source part, automatically turning the light source part off after a predetermined time has elapsed, turning the heat generation part 140 on/off, and selectively driving the light source part 120 or 220 and the heat generation part 140.

Meanwhile, in the lifting band 100 or 200 according to one embodiment of the present invention, both end portions of the band member 110 may be fixed in various ways.

As an example, both end portions of the band member 110 may be coupled directly to each other through a fixing portion 160, 260, or 360 or a separate member in a state in which the band member 110 covers a chin of a user and a front part of a neck.

Specifically, the fixing portions 160, 260, and 360 may include coupling portions 161, 261, and 36 and coupled portions 162, 262, and 362 provided at both end portions of the band member 110, and the coupling portions 161, 261, and 361 may correspond to the coupled portions 162, 262, and 362.

Accordingly, both end portions of the band member 110 may be fixed through a direct coupling between the coupling portion 161, 261, or 361 and the coupled portion 162, 262, or 362.

As an example, the coupling portion 161 and the coupled portion 162 may be a pair of velcros corresponding to each other as shown in FIG. 14.

As another example, the coupling portion 261 and the coupled portion 262 may be a first belt and a second belt which have a certain length as shown in FIG. 15.

In this case, at least one protrusion bar 261a protruding by a certain height may be formed on the first belt, and a plurality of fitting grooves 262a into which the protruding bar 261a may be fitted may be formed in the second belt. The plurality of fitting grooves 262a may be spaced apart from each other by a certain interval in a length direction of the second belt.

Accordingly, a user may fix both end portions of the band member 110 by inserting the protruding bar 261a into any one fitting groove 262a among the plurality of fitting grooves 262a and may adjust a coupling position of the protruding bar 261a and the fitting groove 262a to fit a length of a head of the user.

As another example, as shown in FIG. 16, the coupling portion 361 and the coupling portion 362 may be a belt member including a fitting member 361a protruding from one side of the band member 110 and a plurality of fitting grooves 362a formed in a length direction.

Accordingly, a user may fix both end portions of the band member 110 by inserting the fitting member 361a into any one fitting groove 362a among the plurality of fitting grooves 362a and may adjust a coupling position of the fitting member 361a and the fitting groove 362a to fit a length of a head of a user.

However, the fixing portions 160, 260, and 360 that applicable to the lifting bands 100 and 200 according to one embodiment of the present invention are not limited to forms shown in FIGS. 14 to 16, and as long as two members corresponding to each other are detachably coupled to each other, various known methods may be applied.

Although embodiments of the present invention is described above, the spirit of the present invention is not limited to the embodiments described in the description, and although those skilled in the art may easily provide other embodiments due to addition, change, or removal of the components within the scope of the same spirit of the present invention, such embodiments and the above embodiments are also included in the scope of the spirit of the present invention.

The invention claimed is:

1. A lifting band comprising:
   a band member provided in a plate shape having stretchability and elasticity and having a predetermined area;
   at least one light source part disposed on one surface of the band member and including a plurality of light-emitting diodes (LEDs) configured to, when power is applied, emit light having a certain wavelength band to improve skin;
   a cap member fixed to one surface of the band member to cover the at least one light source part; and
   a heat generation part disposed between the light source part and the cap member to generate heat when power is applied,
   wherein the light source part includes:
   a support member having a plate shape, a certain area, and pliability and an insulating property;
   a plurality of circuit patterns which are not electrically connected to each other, are formed in a plane shape having a certain area, and are attached to one surface of the support member;
   the plurality of LEDs mounted on the plurality of circuit patterns to electrically connect two adjacent circuit patterns; and
   a cover member configured to cover one surface of the support member to cover the plurality of circuit patterns and the plurality of LEDs.

2. The lifting band of claim 1, wherein the circuit pattern is formed of a conductive microfiber web in which a conductive material is plated on a microfiber web.

3. The lifting band of claim 1, wherein:
   the cover member includes a plurality of convex portions protruding outward in a region corresponding to the plurality of LEDs;
   each of the LEDs is accommodated in one of inner spaces of the convex portion corresponding thereto; and
   the inner space of the convex portion has a size that is larger than that of the LED.

4. The lifting band of claim 1, wherein two circuit patterns to which power is applied among the plurality of circuit patterns have a wider area than the other circuit patterns.

5. The lifting band of claim 1, wherein the cap member includes exposure holes formed to pass through regions corresponding respectively to the plurality of LEDs.

6. The lifting band of claim 1, wherein the heat generation part includes:
   a base substrate having a plate shape;
   lead electrode portions formed on one surface of the base substrate and including two lead electrodes not physically connected to each other;
   branch electrode portions including two branch electrodes which extend from the two lead electrodes such that the two branch electrodes are not electrically connected to each other and partial lengths thereof face each other; and
   conductive heat generation materials which have a certain area, are formed to be positioned at overlapping portions of the two branch electrodes facing each other, and when power is supplied, generate heat while electrically connecting the two branch electrodes.

7. The lifting band of claim 6, wherein:
   the heat generation part includes the plurality of branch electrode portions spaced apart from each other by a certain interval in a length direction of the lead electrode, and the plurality of conductive heat generation materials provided respectively on the plurality of branch electrode portions; and
   the plurality of branch electrode portions and the plurality of conductive heat generation materials are disposed to be positioned at positions that do not overlap with the plurality of LEDs provided in the light source part.

8. The lifting band of claim 6, wherein:
   the base substrate includes a film member having an insulating property, and a porous substrate stacked on one surface of the film member; and
   the lead electrode portion and the branch electrode portion are formed on the porous substrate.

9. The lifting band of claim 1, comprising a pair of magnetic terminals for an electrical connection with an external power supply.

10. A lifting band comprising:
    a band member provided in a plate shape having stretchability and elasticity and having a predetermined area;
    at least one light source part disposed on one surface of the band member and including a plurality of light-emitting diodes (LEDs) configured to, when power is applied, emit light having a certain wavelength band to improve skin;
    a cap member fixed to one surface of the band member to cover the at least one light source part; and
    a heat generation part disposed between the light source part and the cap member to generate heat when power is applied,
    wherein the light source part includes:
    a support member having a plate shape, a certain area, a pliability, and an insulating property;

a porous substrate stacked on one surface of the support member;

a plurality of circuit patterns which are not electrically connected to each other, are formed on the porous substrate in a plane shape having a certain area;

the plurality of LEDs mounted on the plurality of circuit patterns to electrically connect two adjacent circuit patterns; and a cover member configured to cover one surface of the support member to cover the circuit patterns and the plurality of LEDs, wherein each of the circuit patterns includes:

a first pattern formed as a printed pattern on the porous substrate such that a conductive material fills pores formed in the porous substrate; and a second pattern attached to one surface of the first pattern.

11. The lifting band of claim 10, wherein the second pattern is formed of a conductive microfiber web in which a conductive material is plated on a microfiber web.

12. The lifting band of claim 10, wherein:

the cover member includes a plurality of convex portions protruding outward from regions corresponding respectively to the plurality of LEDs;

each of the LEDs is accommodated in one of inner spaces of the convex portion corresponding thereto; and the inner space of the convex portion has a size that is relatively larger than that of the LED.

13. The lifting band of claim 10, wherein two circuit patterns to which power is applied among the plurality of circuit patterns have a relatively larger area than the other circuit patterns.

14. The lifting band of claim 10, wherein the cap member includes exposure holes formed to pass through regions corresponding respectively to the plurality of LEDs.

15. The lifting band of claim 10, wherein the heat generation part includes:

a base substrate having a plate shape;

lead electrode portions formed on one surface of the base substrate and including two lead electrodes not physically connected to each other;

branch electrode portions including two branch electrodes which extend from the two lead electrodes such that the two branch electrodes are not electrically connected to each other and partial lengths thereof face each other; and conductive heat generation materials which have a certain area, are formed to be positioned at overlapping portions of the two branch electrodes facing each other, and when power is supplied, generate heat while electrically connecting the two branch electrodes.

16. The lifting band of claim 15, wherein:

the heat generation part includes the plurality of branch electrode portions spaced apart from each other by a certain interval in a length direction of the lead electrode, and the plurality of conductive heat generation materials provided respectively on the plurality of branch electrode portions; and the plurality of branch electrode portions and the plurality of conductive heat generation materials are disposed to be positioned at positions that do not overlap with the plurality of LEDs provided in the light source part.

17. The lifting band of claim 15, wherein:

the base substrate includes a film member having an insulating property, and a porous substrate stacked on one surface of the film member; and the lead electrode portion and the branch electrode portion are formed on the porous substrate.

18. The lifting band of claim 10, comprising a pair of magnetic terminals for an electrical connection with an external power supply.

* * * * *